(12) United States Patent
Wang

(10) Patent No.: US 8,007,835 B2
(45) Date of Patent: Aug. 30, 2011

(54) HIBISCUS ANTHOCYANINS FOR INHIBITING CANCERS

(75) Inventor: Chau-Jong Wang, Taichung (TW)

(73) Assignee: Aiken Biotechnology International Co., Ltd., Chiayi County (TW)

( * ) Notice: Subject to any disclaimer, the term of this patent is extended or adjusted under 35 U.S.C. 154(b) by 0 days.

(21) Appl. No.: 11/959,222

(22) Filed: Dec. 18, 2007

(65) Prior Publication Data

US 2008/0113050 A1 May 15, 2008

Related U.S. Application Data

(62) Division of application No. 11/143,864, filed on Jun. 3, 2005, now abandoned.

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

| 2004/0247619 A1* | 12/2004 | Hambrook ............... 424/195.16 |
| 2005/0100622 A1* | 5/2005 | Nair et al. ..................... 424/777 |
| 2007/0060533 A1* | 3/2007 | Yoshikawa et al. ............. 514/27 |

FOREIGN PATENT DOCUMENTS

WO   WO 2005/040182   *   5/2005

OTHER PUBLICATIONS

Mayo-Clinic, Chronic lymphocytic leukemia, 2008, 8 pages.*
Mayo-Clinic, Leukemia, 2 pages, 2008.*
Types of cancer and cancer treatment in dogs, 7 pages, 2006.*
Puckhaber et al., "Analyses for flavanoid aglycones in fresh and preserved hibiscus flowers", pp. 556-563, 2002.*
Katsube et al. J. agric. Food Chem, 2003, 51, 68-75.*
CAT.INIST, 2003, 2 pages.*
Chang et al., Toxicology and applied phamacology, 205, Dec. 2004, 201-212.*

* cited by examiner

*Primary Examiner* — Michael Meller
(74) *Attorney, Agent, or Firm* — WPAT, P.C.; Anthony King

(57) ABSTRACT

This invention provides a composition for inhibiting cancer cell growth comprising *Hibiscus* anthocyanins extracted from *Hibiscus sabdariffa*. This invention also provides a method for treating cancer comprising administering a patient with an effective amount of *Hibiscus* anthocyanins.

3 Claims, 15 Drawing Sheets

(A)

(B)

HIBISCUS ANTHOCYANINS FOR INHIBITING CANCERS

CROSS-REFERENCE TO RELATED APPLICATIONS

This application is a Divisional of, and claims priority to, U.S. patent application. No. 11/143,864, filed on Jun. 3, 2005, now pending, which is hereby incorporated by reference in its entirety, including the computer readable form of sequence listing filed in such application.

Although incorporated by reference in its entirety, no arguments or disclaimers made in the parent application apply to this divisional application. Any disclaimer that may have occurred during the prosecution of the above-referenced application is hereby expressly rescinded. Consequently, the Patent Office is asked to review the new set of claims in view of all of the prior art of record and any search that the Office deems appropriate.

FIELD OF THE INVENTION

This invention relates to a composition for inhibiting cancers comprising *Hibiscus* anthocyanins.

DESCRIPTION OF PRIOR ART

Nutrition should be given a thorough consideration in cancer prevention because almost a third of all cancer events can be prevented by a change in diet (Doll and Peto, 1981, J. Natl. Cancer Inst. 66: 1191; Willett, 1995, Environ. Health Perspect. 103: 165). Vegetables and fruit are excellent sources of cancer preventive substances. Strong epidemiological evidences suggest that a diet rich in vegetables and fruits can notably reduce the risk for diverse human cancers (Block et al., 1992, Nutr. Cancer 18: 1).

Recent research has identified food compounds (phytochemicals) that may have important anticarcinogenic activities (Mazur and Adlercreutz, 2000, Nutrition 16: 654). Chemopreventive phytochemicals can suppress the initiation or reverse the promotion stage in multistep carcinogenesis. They can also block the progression of precancerous cells into malignant ones (Surh, 2003, Cancer 3: 768). Anthocyanins, which are bioactive phytochemicals, are widely distributed in plants. Anthocyanins not only possess antioxidant ability (Pool-Zobel et al., 1999, Eur. J. Nutr. 38: 227; Tsuda et al., 2000, Biofactors 13: 133), but also mediate other physiological functions related to cancer suppression (Kamei et al., 1995, Cancer Invest. 13: 590; Meiers et al., 2001, J. Agric. Food Chem. 49: 958; Nagase et al., 1998, Planta Med. 64: 216). There has been increasing interest in the pharmaceutical function of anthocyanins.

"Anthocyanin-rich extracts" or "AREs" are extracts derived from foods such as fruits and vegetables that are preferably, semi-purified, purified and/or concentrated such that the water content, sugar content and acid content are reduced and the remaining components are mainly the phenolics including anthocyanins. AREs are known in the art and many are readily available commercially from sources such as Artemis International, Inc. (Madera, Calif.). Concentrated and highly concentrated (about at least 2-3 grams of monomeric anthocyanin per liter or per kg) AREs obtained using standard separation and purification techniques and are also readily commercially available in the form of powders and liquids.

Recent studies have shown molecular evidence of cancer chemoprevention by anthocyanins. The mechanisms can be grouped into three aspects: (i) antioxidation, (ii) molecular mechanisms related to anticarcinogenesis, and (iii) molecular mechanisms involved in apoptosis induction in tumor cells (Hou, 2003, Curr. Mol. Med. 3: 149). It has been reported that anthocyanins exhibited inhibitory effects on the growth of several cancer cells (Karnei et al., 1995, Cancer Invest. 13: 590; Meiers et al., 2001, J. Agric. Food Chem. 49: 958; Nagase et al., 1998, Planta Med. 64: 216), antioxidative effects (Pool-Zobel et al., 1999, Eur. J. Nutr. 38: 227; Tsuda et al., 2000, Biofactors 13: 133), and anticarcinogenic effect in 1,2-dimethylhydrazine-initiated F344/DuCrj rats (Hagiwara et al., 2002, J. Toxicol. Sci. 27: 57). An invention discloses that the anthocyanin-rich extracts from chockeberry, bilberry and grape can be used to inhibit colon carcinoma cell (US patent application No. 2005013880).

*Hibiscus sabdariffa* L. belongs to the Malvaceae family. The calyces of *Hibiscus* have been used in traditional medicine. *Hibiscus* flowers contain gossypetin, glucoside, bibiscin, *Hibiscus* anthocyanin, and *Hibiscus* protocatechuic acid and have the following effects, choleretic and diuretic functions, decreasing blood pressure, reducing the viscosity of the blood, and stimulating intestinal peristalsis (Ali et al., 1991, J. Ethnopharmacol. 31: 249). Thus, the dried flowers of *Hibiscus sabdariffa* are a functional natural product with a chemopreventive capacity.

Previous studies have shown that *Hibiscus* anthocyanins (HAs) (which are extracted from the dried calyx of *Hibiscus sabdariffa*) possess antioxidant bioactivity both in vivo and in vitro (Tseng et al., 1997, Food Chem. Toxicol. 35: 1159; Wang et al., 2000, Food Chem. Toxicol. 38: 411).

There remains a need for identifying natural compounds, phytochemicals and food extracts that are effective as chemopreventatives against cancer, including leukemia. The present inventors have discovered that compositions comprising *Hibiscus* anthocyanins (HAs) extracts are effective for inhibiting cancer cell growth, and have further discovered methods for specifically inhibiting the growth of leukemia cells without inhibiting the growth of normal leukemia.

AM), and then incubated for 24 h with HAs (3 mg/ml). DMSO (0.25%) served as solvent control. Quantitative assessment of the percentage of HL-60 cells in sub-G1 and G0/G1 phases was indicated by propidium iodide (PI). Quantitative analysis of apoptosis was determined by flow cytometry assay.

Figure 5:
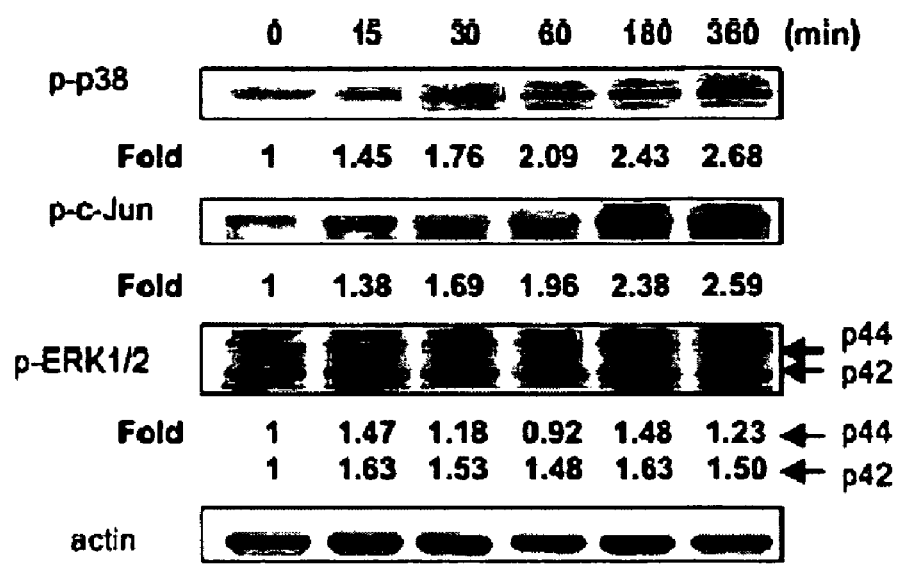

FIG. 5 shows HAs activating MAP kinases in a time-dependent manner. HL-60 ($1 \times 10^6$ cells/dish) was incubated with HAs (3 mg/ml) for various durations (0-360 min). Protein extracts were prepared at the incubated time points to assess the activation of MAP kinases. The levels of phosphorylated MAP kinases (p38, ERK1/2, and c-Jun) were determined by Western blotting using specific antibodies. Actin, load controls. This figure is a representative of three independent experiments with similar results.

Figure 6:
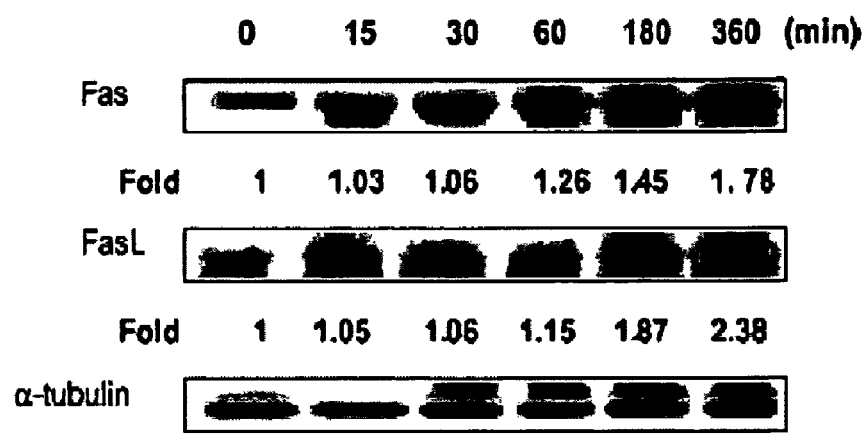
Figure 6:
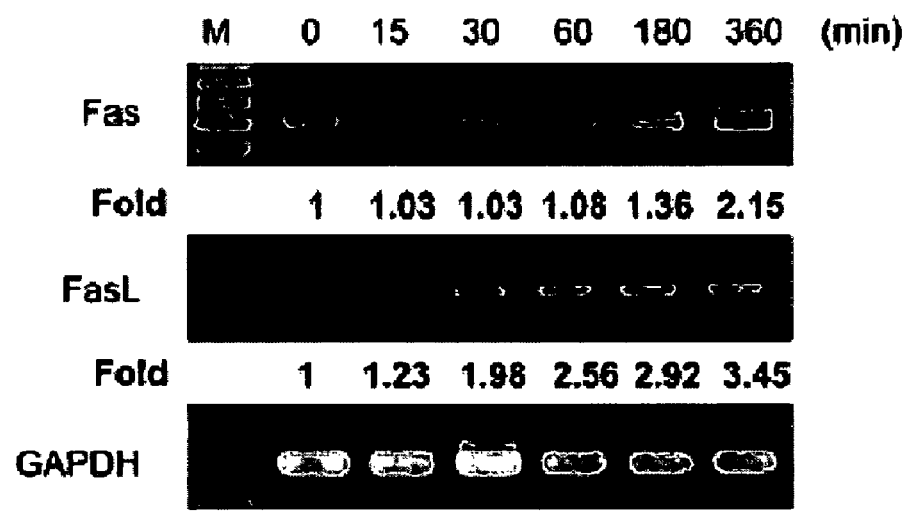

FIG. 6 shows time course of HAs-induced Fas and FasL activation in HL-60 cells. HL-60 cells were treated with HAs (3 mg/ml) for the time indicated and assayed for Fas, FasL activation, and mRNA expression. (A) Untreated control cells were run in parallel in the same gel. The proteins were analyzed using Western blotting. α-Tubulin, load controls. (B) Total RNA was extracted at each time point, Fas and FasL mRNA expressions were analyzed by RT-PCR. M, molecular weight marker. GAPDH, loading controls. This figure is a representative of three independent experiments with similar results.

Figure 7:
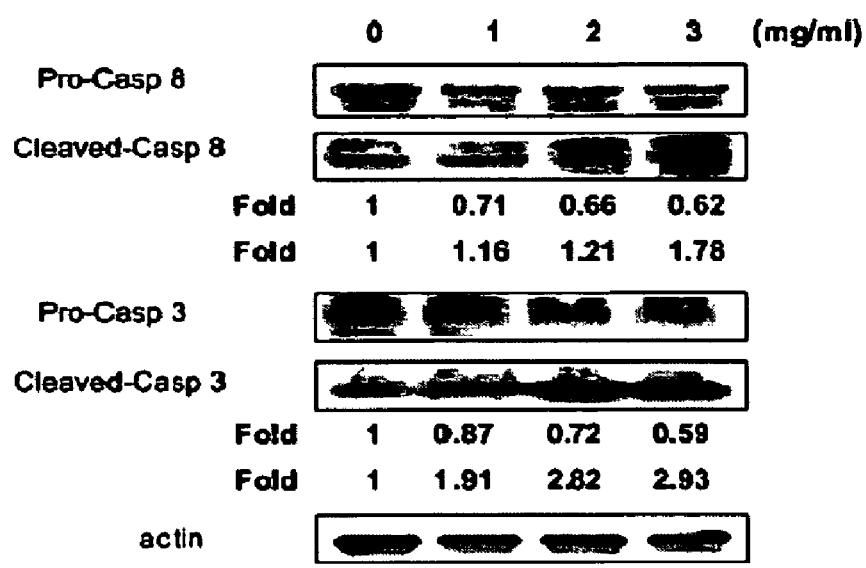

FIG. 7 shows involvement of caspase-8 and caspase-3 in HAs-induced apoptosis. The levels of cleaved caspase-8/-3 and pro-caspase-8/-3 proteins in HL-60 cells with HAs treatments were determined. Cells were treated with HAs (360 min) for the indicated concentration and analyzed using immunoblotting with anti-cleaced-caspase-8/-3 and pro-caspase-8/-3 antibody. Actin and a-tubulin were the loading controls. This figure is a representative of three independent experiments with similar results.

Figure 8:
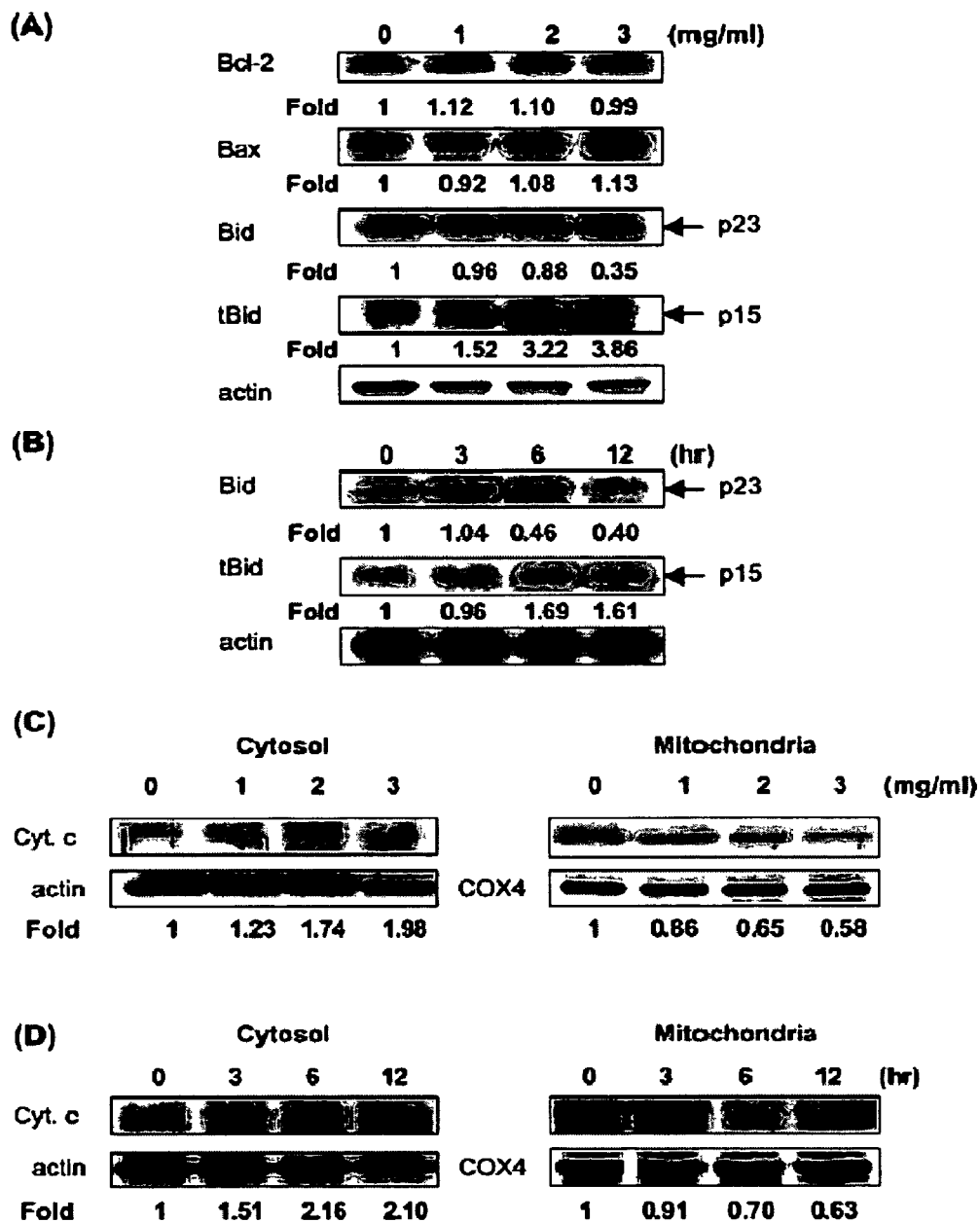

FIG. 8 shows effect of HAs-induced Bid activation and cytochrome c release. (A) HL-60 cells were treated with HAs (360 min) for the indicated concentration and analyzed by immunoblotting with anti-Bcl-2, Bax, and Bid antibody. The arrows indicate the position of full-length Bid (p23) and the p15 truncated form of active Bid (tBid). Actin was the loading control. (B) HL-60 cells were treated with HAs (3 mg/ml) for the indicated times and analyzed by immunoblotting with anti-Bid antibody. (C) HL-60 cells were treated with HAs (360 min) for the indicated concentration, and the expression of cytochrome c in the cytosol and the mitochondria of the untreated and HAs-treated HL-60 cells was assayed by immunoblotting. (D) HL-60 cells were treated with HAs (3 mg/ml) for the indicated times, and the expression of cytochrome c, cytochrome oxidase subunit IV(COX4), a mitochondrial marker served as a protein loading control, was determined. This figure is a representative of three independent experiments with similar results.

Figure 9:
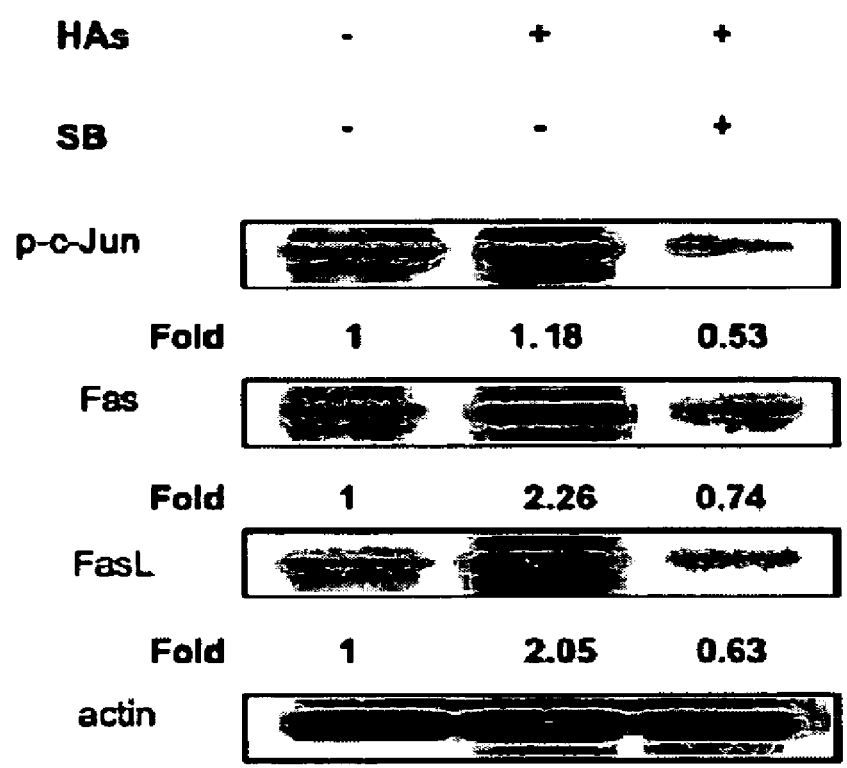

FIG. 9 shows effect of p38 MAPK inhibitor (SB203580) on HAs-induced apoptosis in HL-60 cells. Cultured cells were treated in the absence or presence of SB203580 (50 µM, 24 h preincubation) with HAs (3 mg/ml) for 6 h, and phospho-c-Jun, Fas, and FasL expressions were analyzed by Western blotting. Actin was used as the loading control. This figure is a representative of three independent experiments with similar results.

Figure 10:
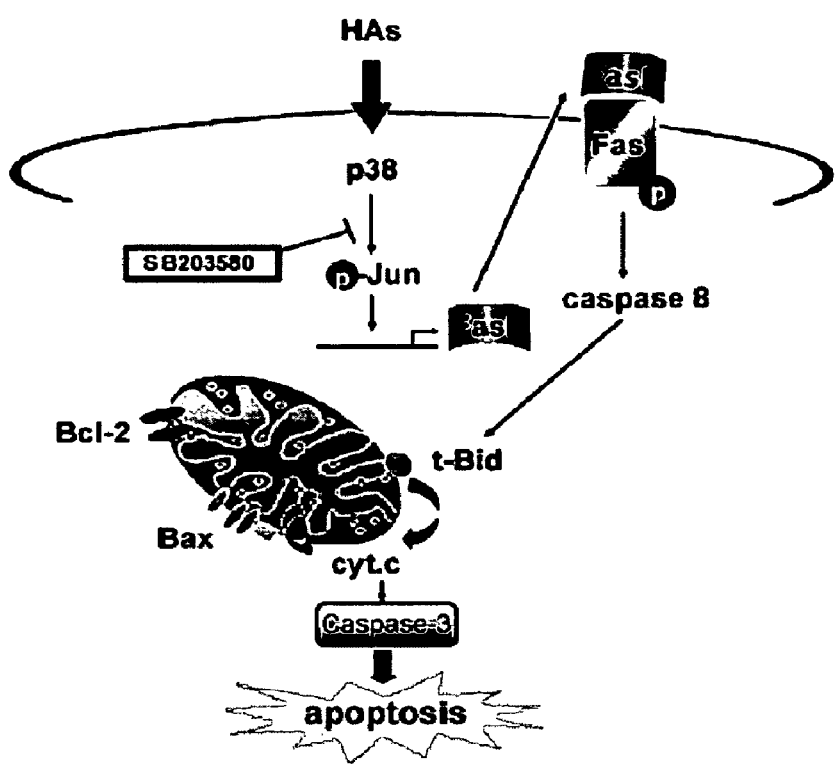

FIG. 10 shows the model showing pathways that mediate HAs-induced apoptosis in HL-60 cells. HAs were been shown to be capable of inducing HL-60 cell apoptosis. p38 signaling activation involves mitochondrial membrane alterations resulting in the release of cytochrome c and caspases activation.

Figure 11:
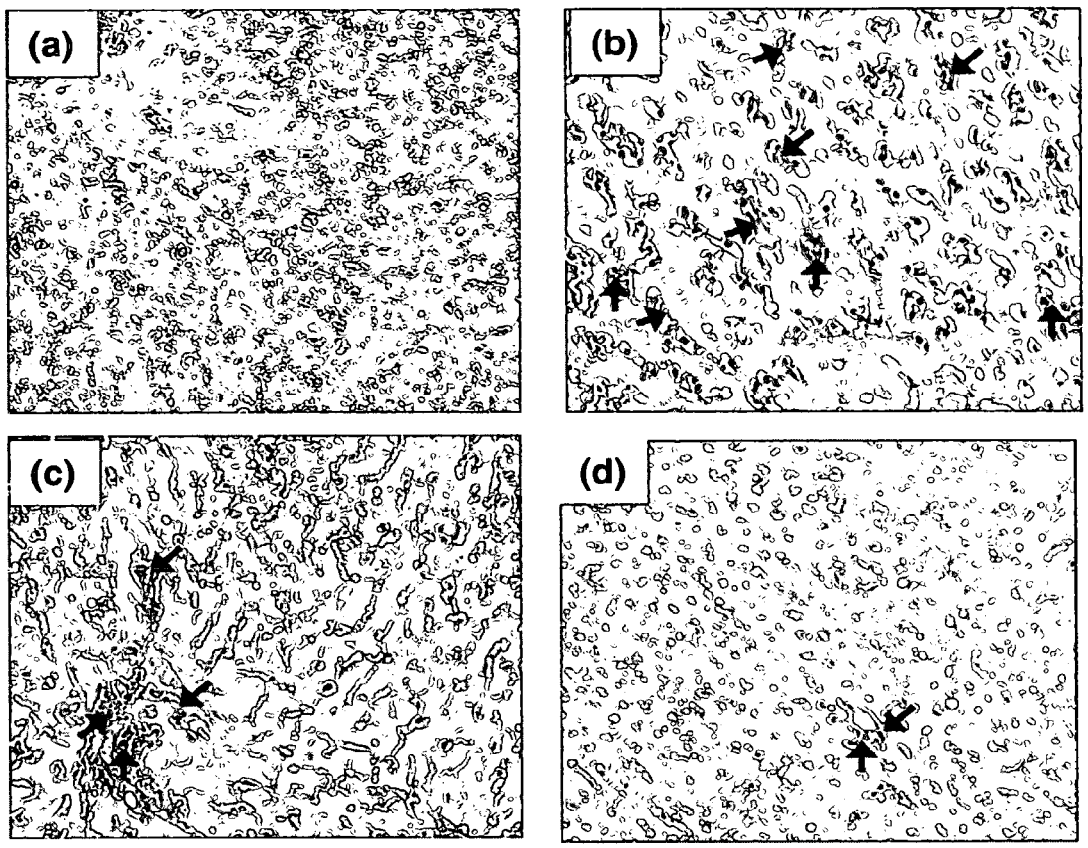

FIG. 11 shows pathological analysis of rat liver using H&E stain. (a) normal control, (b) the animal were treated with NMU alone (35 mg/kg), (c) NMU and HAs (0.1%), and (d) NMU and HAs (0.2%). The arrow indicates leukemia cells invaded in liver tissue. The amplification factor is 100×.

Figure 12:
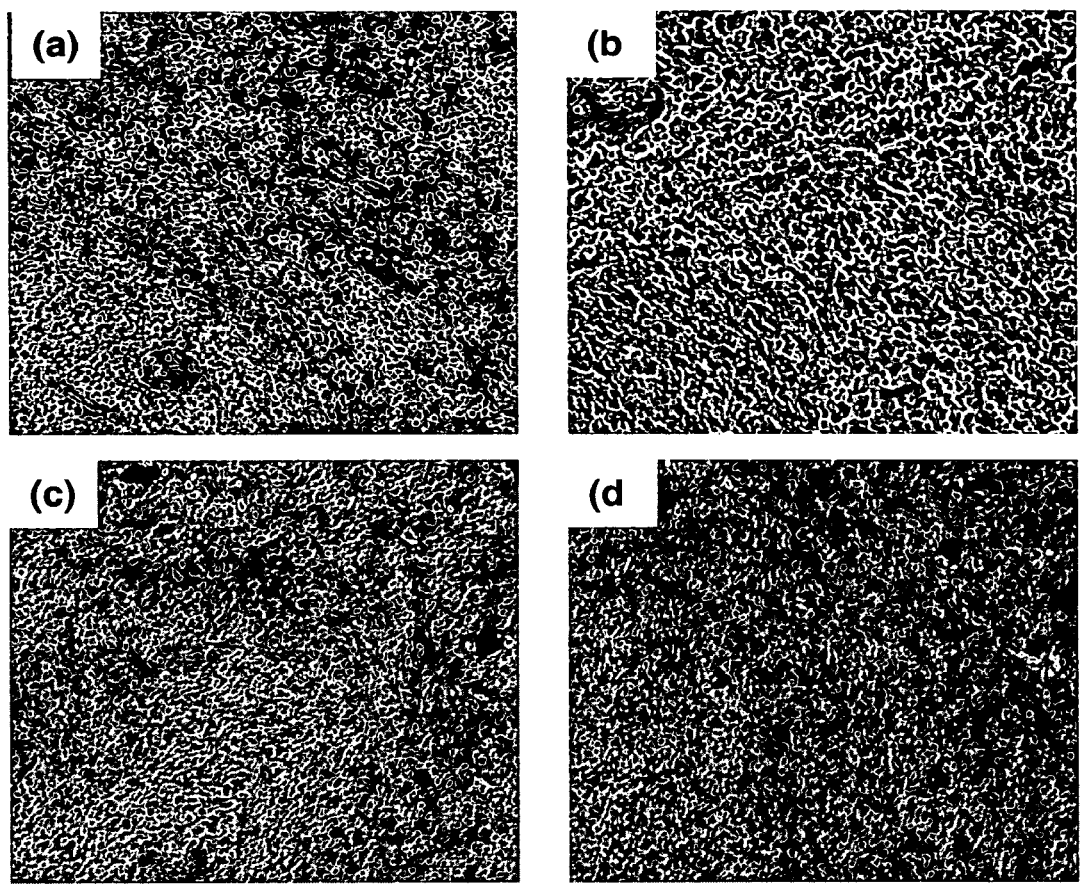

FIG. 12 shows pathological analysis of rat spleen was using H&E stain. (a) normal control, (b) the animal were treated with NMU alone (35 mg/kg), (c) NMU and HAs (0.1%), (d) NMU and HAs (0.2%). The leukemia cells invaded in spleen red pulp tissue. The amplification factor is 100×.

Figure 13:
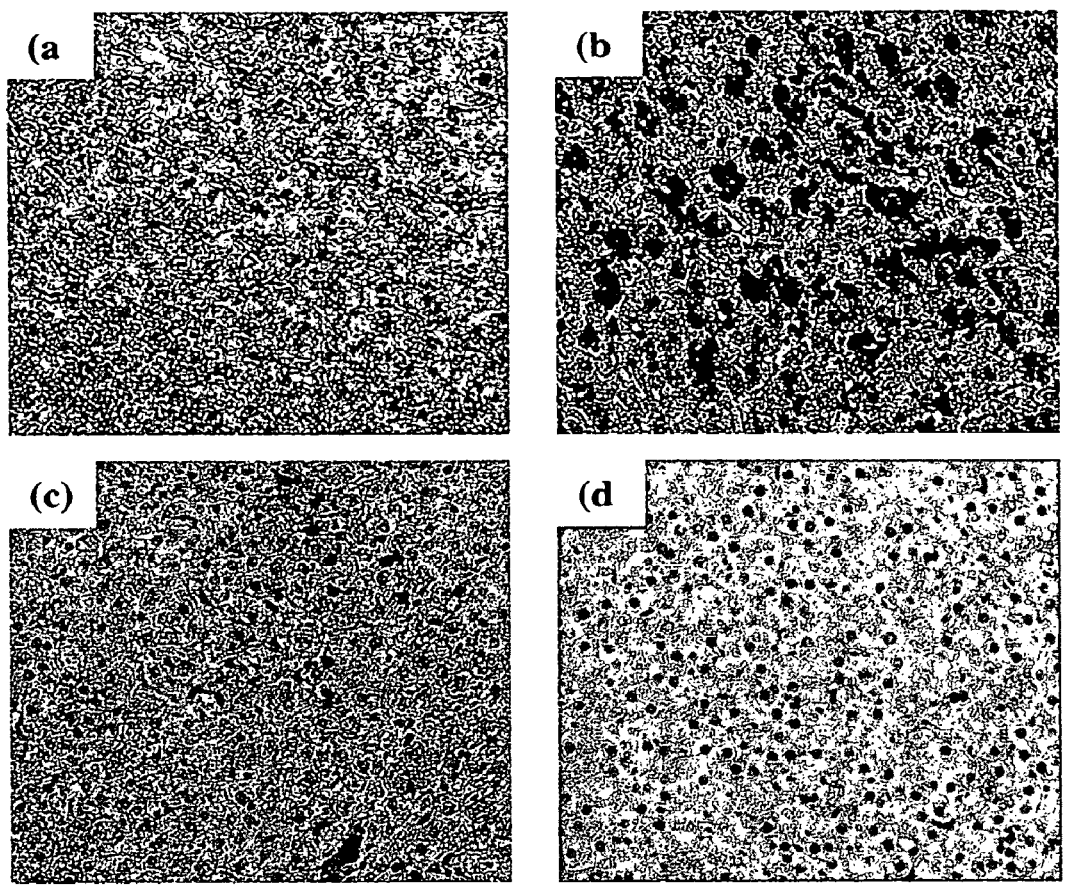

FIG. 13 shows pathological analysis of rat liver was using Myeloperoxidase stain. (a) normal control, (b) the animal were treated with NMU alone (35 mg/kg), (c) NMU and HAs (0.1%), (d) NMU and HAs (0.2%). The amplification factor is 100×.

Figure 14:
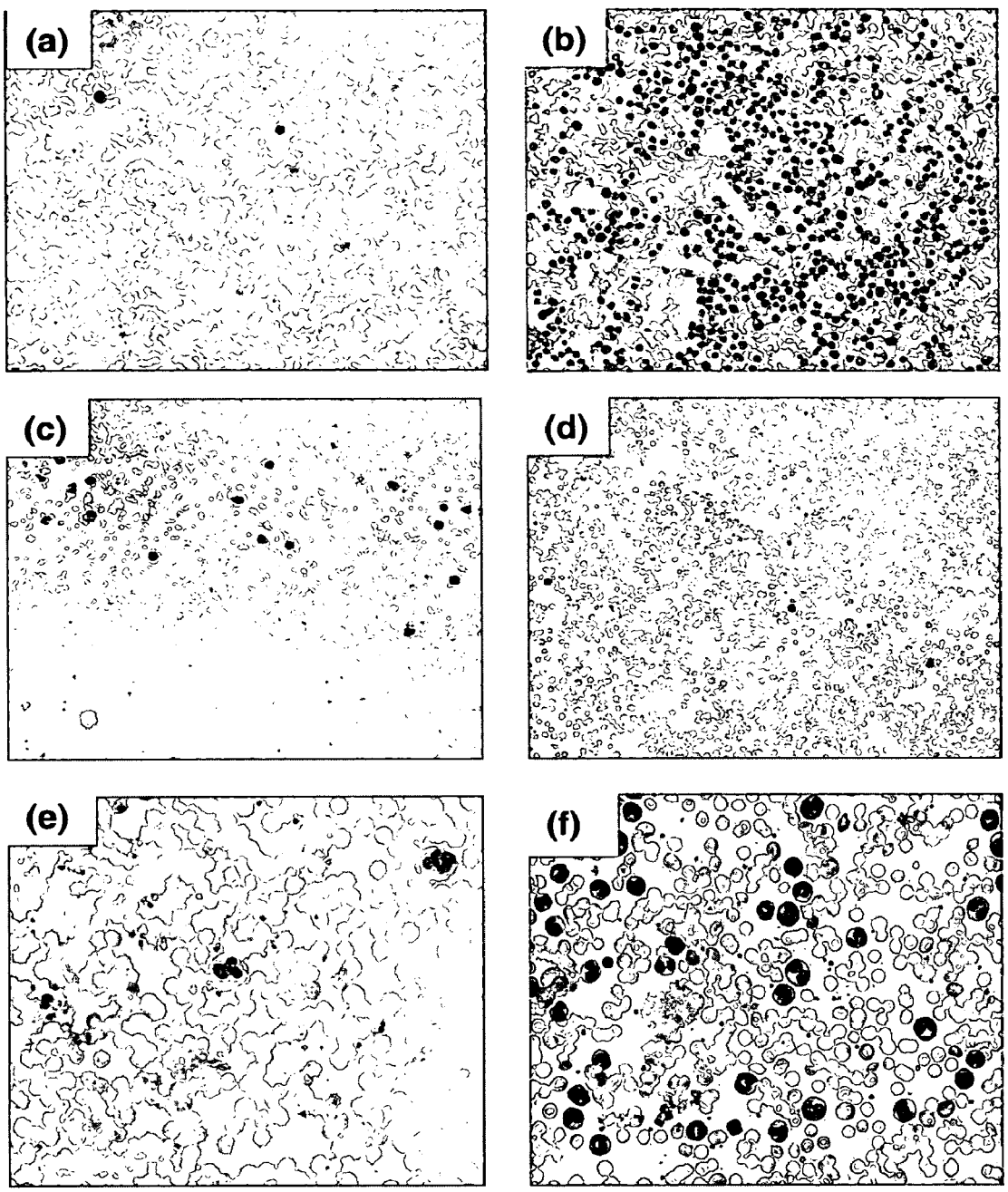

FIG. 14 shows morphology analysis of rat whole blood was using Liu's stain. (a) normal control, (b) the animal were treated with NMU alone (35 mg/kg), (c) NMU and HAs (0.1%), (d) NMU and HAs (0.2%), (e) normal control, and (f) the animal were treated with NMU alone (35 mg/kg). The amplification factor of (a) to (d) is 40×, and the amplification factor of (e) and (f) is 100×.

Figure 15:
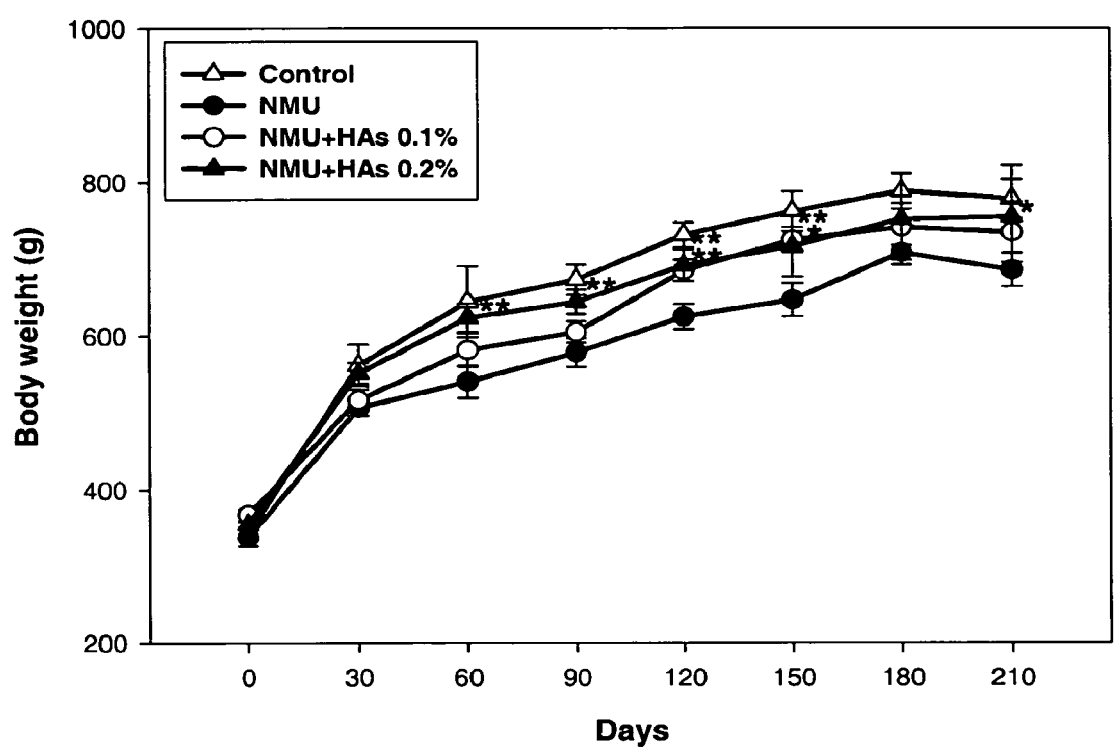

FIG. 15 shows the body weight of the animals in experiment. Every 30 days record one times. *$p<0.05$; *$p<0.005$, compared with NMU-treated group. Final survival number of control group was 12 rats; NMU only group was 7 rats; NMU+HAs 0.1% group was 9 rats; and NMU+HAs 0.2% group was 11 rats.

SUMMARY OF THE INVENTION

This invention provides a composition for inhibiting cancer cell growth comprises *Hibiscus* anthocyanins (HAs).

This invention also provides a method for treating cancer comprising administering a patient with an effective amount of *Hibiscus* anthocyanins.

DETAILED DESCRIPTION OF THE INVENTION

Figure 1:
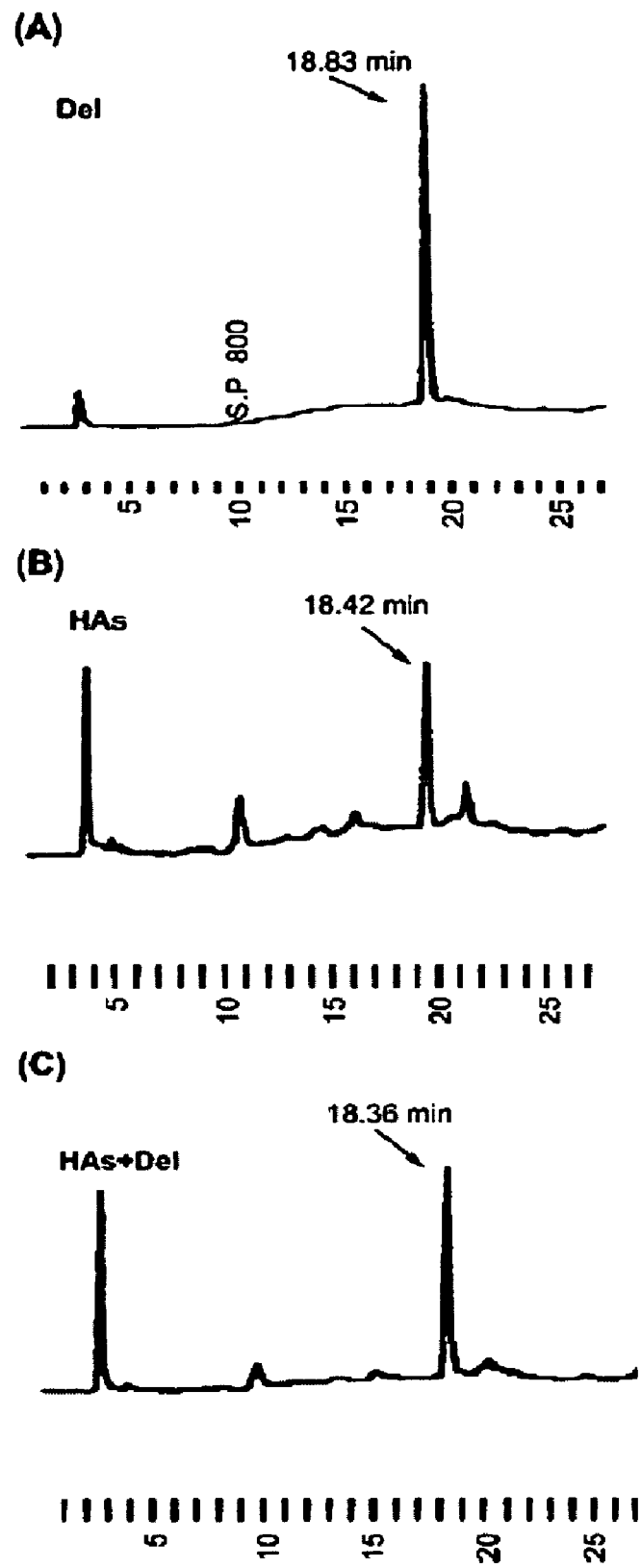
FIG. 1 shows delphinidine content of HAs analyzed by HPLC. In this figure, (A) Standard is delphinidine (0.1 mg/ml; 10 µl); (B) HAs extract (1 mg/ml; 10 µl); and (C) HAs (1 mg/ml; 5 µl)+delphinidine (0.1 mg/ml; 5 µl).

This invention provides a composition for inhibiting cancer cell growth comprising *Hibiscus* anthocyanins (HAs). In a preferred embodiment, the *Hibiscus* is Roselle, *Hibiscus sabdariffa*. The plant tissue such as leaf, stem, flower or fruit can be used to extract HAs. Because the flower and calyx of Roselle contain high concentration of HAs, the HAs are prepared from the flower or calyx of the Roselle in this invention. The HAs are characterized by HPLC shown in FIG. 1.

Several methods for extracting anthocyanins are well known, such as supercritical fluid, water extraction, solvent extraction etc. In a preferred embodiment, the HAs are extracted from the flower or calyx of the Roselle by methanol. In this invention, the anthocyanins-rich extract from the Roselle is analyzed by HPLC, and the result shows that the HAs comprise delphindin and cyaniding, at least.

The *Hibiscus* anthocyanins in the invention could be extracted by water or organic solvent. The organic solvent includes but is not limited to alcohol (such as $CH_3OH$, $C_2H_5OH$, $C_3H_7OH$), ester (such as acetyl acetate), alkane (such as hexane) and halogenated alkane (such as $CH_3C_1$, $C_2H_2Cl_2$). The preferred organic solvent is ethanol or alcoholic solvent without causing any side effect of human. The most preferred organic solvent is methanol.

The subject accepting the mixture of the invention includes but is not limited to human, mammal, mouse, rat, horse, pig, chicken, duck, dog and cat.

The HAs preparation method is not limited by the following description. The known methods can be used to extract HAs. In this invention, the HAs are prepared by a method comprising: (a) incubating Roselle with methanol, (b) concentrating the incubation under reduced pressure, and (c) eluting the precipitate with methanol, wherein the methanol contains 0.1% HCl. In a preferred embodiment, the step (a) is at low temperature such as 4, and the step (a) is at room temperature such as 25

The HAs can induce the apoptosis of the cancer cell in accordance with this invention. The cancer cells include abnormal cancer cells associated with lymphoma, leukemia, plasma cell dyscrasias, multiple myeloma, amylodosis, also as known as hematopoietic tumors, colorectal cancer, ovarian cancer, bone cancer, renal cancer, breast cancer, gastric cancer, pancreatic cancer, or melanoma. Preferably, the cancer cell is leukemia cell, and the growth and cell cycle progression of the leukemia cells are inhibited by the composition of this invention. In a preferred embodiment, the leukemia cell is human leukemia cell.

In this invention, the human promyelocytic leukemia cells (HL-60) are used as the target cells, served as a useful model for testing antileukemic or general antitumoral compounds (Suh et al., 1995, Anticancer Res. 15: 233). The HL-60 cells exhibit the strongest HAs cytotoxicity potency. The mechanism by which HAs caused apoptotic death in human myeloid leukemic HL-60 cells is also elucidated. The *Hibiscus* anthocyanins induce HL-60 apoptosis, which is via p38-FasL signaling pathway and Bid pathway. Further, the p38 signaling pathway acts at an early step prior to the cytochrome c release and caspase activation.

The *Hibiscus* anthocyanins can be used to inhibit cancer cell growth. In particular, the HAs can be used to induce apoptosis of cancer cells. There are several signaling pathways involved in the HAs-inducing apoptosis mechanisms. In this invention, the HAs activate the Caspase 8 pathway, Caspase 3 pathway, p38 MAP kinase pathway, c-Jun kinase pathway, or Bid pathway. The HAs can stimulate the cytochrome c release from mitochrondrial of cancer cell. These pathways can act alone or combined.

This invention also provides a method for treating cancer comprising administering a patient with a composition comprising HAs. The composition further comprises a pharmaceutical acceptable carrier. In a preferred embodiment, the cancer is leukemia. The HAs are characterized by HPLC shown in FIG. 1. For treating leukemia, the effective amount of the composition *Hibiscus* anthocyanins is 0.5~5.0 mg/ml. In a preferred embodiment, the effective amount is 3.0 mg/ml.

The administration route of HAs to a patient is via injection, oral or external application. In a preferred embodiment for treating leukemia, the administration route to a patient is via injection.

EXAMPLE

The following examples are offered by way of illustration and not by way of limitation.
Materials Used in this Invention SB203580 (4-[4-fluorophenyl]-2-[4-methylsulfinylphenyl]-5-[4-pyridyl]-1H-imidazole), PD098059 (2-[2-amino-3-methoxyphenyl]-4H-1-benzophyran-4-one), SP600125 (1,9-pyrazoloanthrone), wortmannin were purchased from Sigma (St. Louis, Mo., USA). These inhibitors were stored in dimethyl sulfoxide (DMSO) and added to the culture medium to a final concentration as described in the figure legends. However, the amount of DMSO in the cell culture medium did not exceeded 0.3% upon drug treatment. Polyclonal antibody against phospho-p38 MAP kinase (Thr180/Tyr182) and phospho-c-Jun (Ser-73) were purchased from Cell Signaling Technology (Beverly, Mass., USA). Antibody against p-ERK (E-4), FAS (FL-335), FASL (C-178), caspase-8 (H-134), caspase-3 (H-277), BID (C-20), Bcl-2 (N-19), Bax (P-16), and cytochrome c (A-8) were purchased from Santa Cruz Biotechnology (Santa Cruz, Calif., USA). Monoclonal mouse antibody with reactivity to human cytochrome oxidase subunit IV was purchased from Molecular Probes (Eugene, Oreg., USA). Horseradish peroxidase-conjugated anti-mouse secondary antibodies were purchased from NEN Life Science Products, Inc. (Boston, Mass., USA). Anti-rabbit, anti-actin, and anti-a-tubulin secondary antibodies were purchased from Sigma.

Example 1

Preparation of *Hibiscus* Anthocyanins

HAs were prepared from the dried flower of *Hibiscus sabdariffa* L. (20 g) with methanol (2 l) containing 1% HCl for 1 day at 4. The extract was filtered and then concentrated under reduced pressure at 25. The precipitate was collected, stood on an Amberlife Diaion HP-20 resin column for 24 h, and then cleaned with distilled water (5 l) containing 0.1% HCl solution and eluted with methanol. The filtrate was collected and then lyophilized to obtain approximately 2 g of HAs and stored −20 before use.

Example 2

HPLC Assay for HAs

Total anthocyanins were extracted using the Fuleki and Francis (1968, J Food Sci. 33: 78) method. In particular, 100 Al of HAs (10 mg/ml) were diluted to 3 ml with the pH 1.0 and 4.5 buffers, respectively. The O.D. of the sample was measured at 535 nm, using distilled water as blank. The difference in O.D. was obtained by subtracting the total O.D. at pH 4.5 from that at pH 1.0. Both values were calculated from the O.D. readings using the appropriate dilution and calculation factors. For the standardization of HAs, delphinidine in HAs were determined by HPLC using a symmetry shield RP18 column (3.5 μm, 4.6×150 mm) and a UV/visible detector (monitored at 530 nm). The mobile phase was consisted of $H_2O$ and 10% formic acid/methanol (65/35, v/v). The sample (1 mg) was dissolved in 1 ml acidic methanol (HCl—H3OH=1:1, v/v) and boiled at 95 for 30 min, and 10 μl of which was injected into chromatography. The flow rate was set at 1 ml/min. The result was evaluated with the commercially available standard delphinidine.

Spectrophotometer analysis of HAs showed that the purity of HAs were approximately 85-95%. For HAs standardization, delphinidine contained in the HAs was determined using HPLC. Pure delphinidine showed a retention time of 18.83 min (FIG. 1A). HPLC analysis of HAs exhibited a peak at 18.42 min (FIG. 1B), which was merged with that of delphinidine standard at 18.36 min (FIG. 1C). The data confirmed that delphinidine is the major component in the *Hibiscus sabdariffa* L. anthocyanin, consisting of approximately 3-4% of HAs in each analysis.

Example 3

(A) Cell Line and Cell Culture

Human gastric carcinoma AGS was maintained in F-12 Nutrient Mixture medium; mouse NIH/Swiss embryo cells, hepatocellular carcinoma Hep 3B, and colorectal adenocarcinoma Caco-2 were maintained in DMEM; and hepatoblastoma HepG2, adenocarcinoma MCF-7, and human oral epidermoid carcinoma KB were maintained in MEM. HL-60 cell line, a model of human promyelocytic leukemia (Collins et al., 1977, Nature 270: 347), was cultured in suspension in RPMI 1640 medium (Gibco, Grand Island, N.Y., USA) supplemented with 10% fetal calf serum (FBS) and antibiotics (100 units/ml of penicillin and 100 μg/ml of streptomycin). Incubation was carried out at 37 in a humidified atmosphere of 5% $CO_2$ and 95% air. Cells were passaged thrice a week to maintain logarithmic growth. Cell viability, as determined by trypan blue exclusion, was greater than 95%.

(B) Cytotoxicity of HAs on HL-60 Cells

Cells were seeded at a density of $5 \times 10^4$ cells/well and cultured with various concentrations (0, 0.05, 0.1, 0.2, 0.5, 1, 3, 4 mg/ml) of HAs for 24 h or treated with HAs (3 mg/ml) for various periods of time (0, 12, 24, 48 h). Thereafter, the medium was changed and 3-(4,5-dimethylthiazol-zyl)-2,5-diphenyltetrazolium bromide (MTT; 0.1 mg/ml) (Sigma) was added for 4 h. The viable cell number is directly proportional to the production of formazan, which was dissolved in isopropanol and measured spectrophotometrically at 563 nm. The percentage of viable cells estimated by comparison with untreated control cells.

Cell viability was assayed in cultures exposed to 0.05-4.0 mg/ml HAs for 24 h and showed a concentration dependent inhibitory effect on the growth of NIH3T3, Hep G2, MCF-7, KB, Caco-2, Hep 3B, HL-60, and AGS cells. The strongest cytotoxicity of HAs was found in human leukemia HL-60 cells. The results also showed less cytotoxicity toward normal cells (NIH3T3 cells).

The influence of HAs on the human leukemia HL-60 cell growth process is investigated by using the MTT assay. HL-60 cells were incubated with 0.05-4.0 mg/ml HAs for 24 h, or with 3 mg/ml of HAs for various periods of time (0, 12, 24, 48 h). The concentration of HAs inhibiting 50% of HL-60 cell viability (IC50) was around 2.49 mg/ml (FIG. 2A). Treatment with HAs (3 mg/ml) for 0-48 h, an approximate 75% of decrease in cell number was observed at 24 h (FIG. 2B). Morphological examination showed that HAs-treated cells expressed typical apoptosis characteristics, including membrane blebbing, cell shrinkage, and apoptotic bodies.

Example 4

(A) Analysis of Cell Cycle and Quantification of Apoptosis

Flow cytometric analysis of HL-60 cells was performed on the 24-h cultures using a FACScan. The cells of harvest were centrifuged at 1000 rpm for 5 min at room temperature. Thereafter, cells were washed once with Tris-buffered saline (TBS). Then cell suspension was centrifuged again (1000 rpm, 5 min) and resuspended in 70% ethanol. After incubation at −20 for at least 24 h, the cells were resuspended in 1 ml of cell cycle assay buffer [50 μg/ml propidium iodide (PI), 50 μg/ml RNase A, and 0.1% Triton X-100], and it was incubated for 15 min in darkness. Propidium iodide (Sigma) was excited at 488 nm, and fluorescence signal was subjected to logarithmic amplification with PI fluorescence (red) being detected above 600 nm. Cell cycle distribution is presented as the number of cells versus the amount of DNA as indicated by the intensity of fluorescence, and the extent of apoptosis was determined by counting cells of DNA content below the G0/G1 peak.

(B) Dose- and Time-Dependent HAs-Induced Apoptosis in HL-60 Cells

Figure 2:
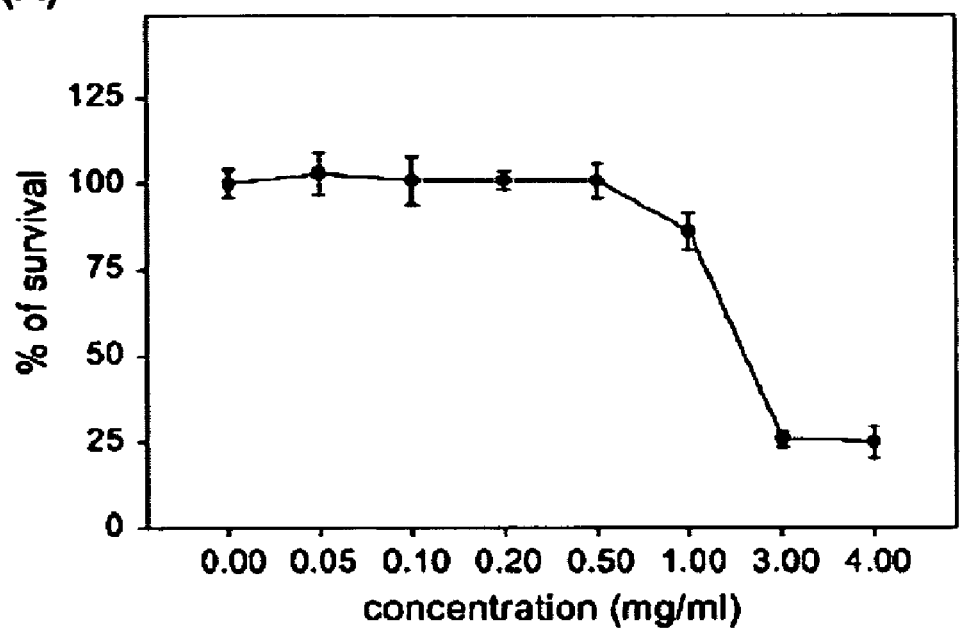
FIG. 2 shows induction of cell death by HAs. HL-60 cells ($5 \times 10^4$ cells/well) treated with various concentrations (0-4 mg/ml) of HAs for 24 h (A) or treated with 3 mg/ml of HAs for the indicated times (B). The survival cell number is directly proportional to formazan, which was measured spectrophotometrically at 563 nm. The value are means±SD, n=3.
Figure 2:
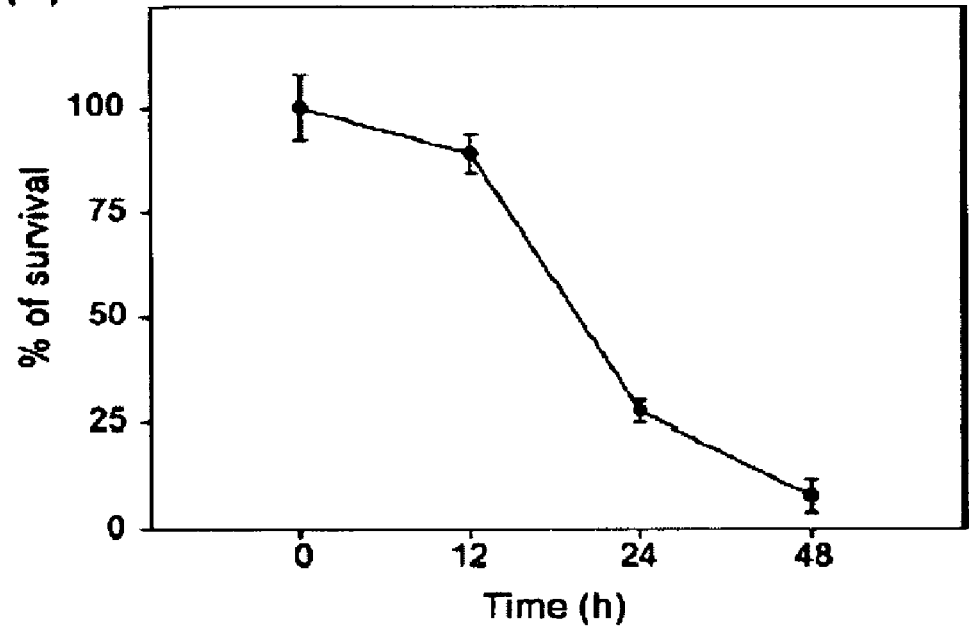
Figure 3:
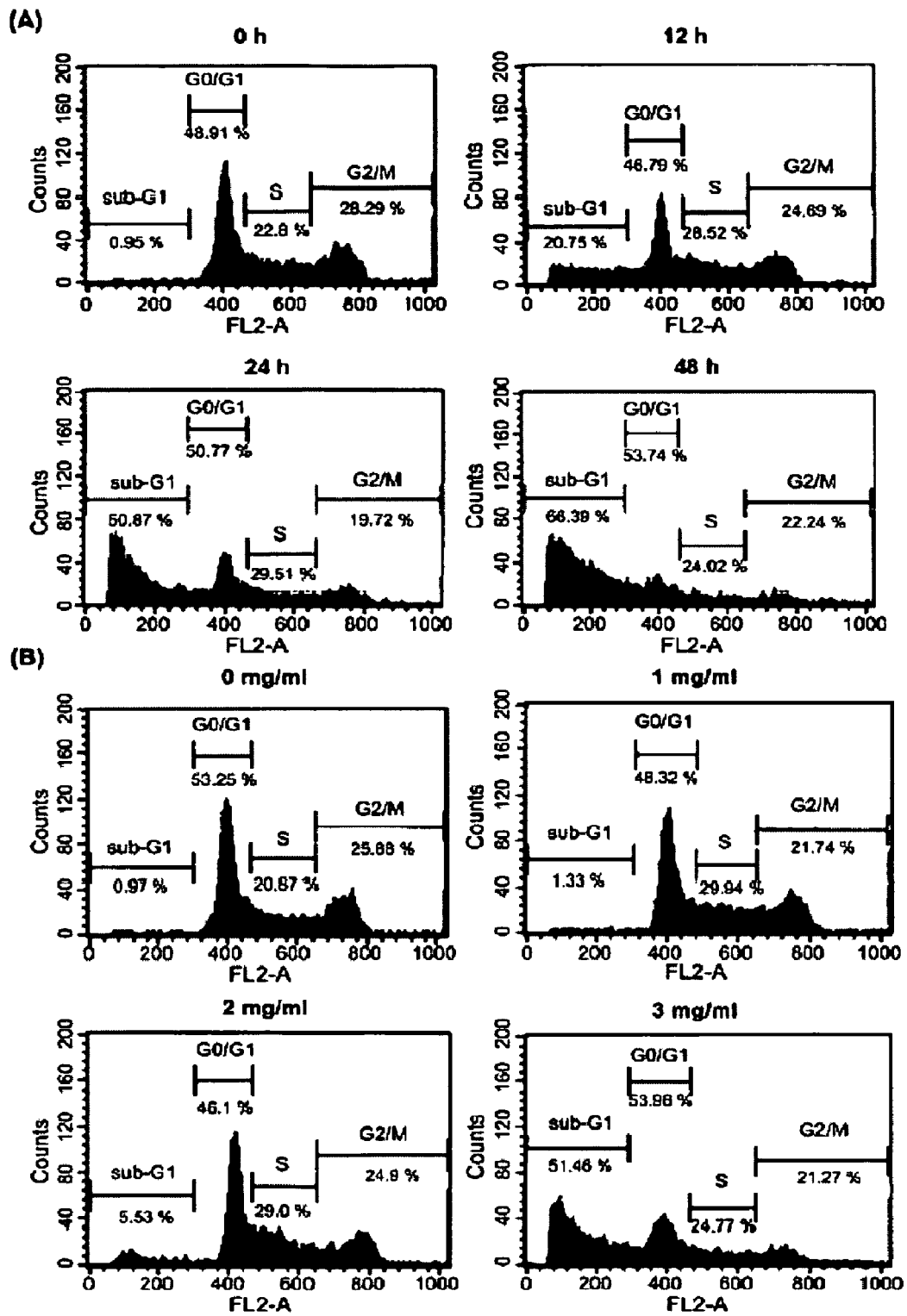
FIG. 3 shows the effects of HAs on HL-60 cell cycle distribution. HL-60 cells treated with 3 mg/ml of HAs for indicated time (A), or with various concentrations (0-3 mg/ml) of HAs for 24 h (B). The DNA content was analyzed using fluorescence flow cytometry. The position of the sub-G1 peak (hypodiploidy), integrated by apoptotic cells, and the G0/G1 and G2/M peaks are indicated. Quantitative assessment of the percentage of HL-60 cells in the sub-G1 and G0/G1 phases was indicated by propidium iodide (PI). The experiment was repeated three times and the representative histograms are shown.

As shown in FIG. 2, HAs have presented an inhibitory effect on the growth of HL-60 cells. The exposure HAs caused a clear cellular ladder-like pattern of DNA fragments, a characteristic of apoptosis (data not shown). The HAs-induced apoptotic effect was confirmed with flow cytometry. When cells were treated with HAs (3 mg/ml) for various periods of time (0, 12, 24, and 48 h), an apparent accumulation of cells in the sub-G1 phase (from 0.95% to 66.39%) (hypodiploid phase) was observed (FIG. 3A). It was found that HL-60 cells exposed to 0, 1, 2, and 3 mg/ml HAs for 24 h demonstrated 0.97%, 1.33%, 5.53%, and 51.46% apoptosis, respectively. This was more than a 50% increase in apoptotic cells (FIG. 3B). Therefore, HAs have stimulated a time- and concentration-dependent increase in HL-60 cells. These data indicated that HAs were cytotoxic to HL-60 cells.

Example 5

(A) Western Blot Analysis

To analyze of the expression of proteins, HAs (0, 1, 2, 3 mg/ml) were added to the culture for 24 h, or cells were treated with HAs (3 mg/ml) for various periods of time (0, 15, 30, 60, 180, 360 min). The medium was removed, and the cells were rinsed with TBS at room temperature. Then 500 μl of cold RIPA buffer (1% NP-40, 50 mM Tris-base, 0.1% SDS, 0.5% deoxycholic acid, and 150 mM NaCl, pH 7.5) with three kinds of proteinase freshly added (10 μg/ml leupeptin, 10 μg/ml PMSF, and 17 μg/ml sodium orthovanadate) were used. After sonication for 1 h at 4° C., a centrifugation (10,000×g) of cell lysate was performed for 10 min at 4° C. The supernatant (50 μg protein) was mixed with an equal volume of electrophoresis sample buffer and boiled for 10 min, which was then subjected to SDS-polyacrylamide gel electrophoresis using a 10% running gel, and electroblotted to nitrocellulose membranes (Millipore, Bedford, Mass., USA). Nonspecific binding was blocked by incubation of the membrane with TBS containing 1% (W/V) nonfat dry milk and 0.1% (v/v) Tween-20 (TBST) for more than 2 h. Membranes were washed with TBST three times for 10 min and incubated with appropriate dilution of primary antibody in TBST for 2 h. Membranes were then extensively washed with TBST before being incubated with appropriate horseradish peroxidase-conjugated secondary antibody for 1 h. After washing the membrane three times, 10 min each in TBST, detection was performed using ECLWestern blotting detection reagents (Amersham, Arlington Heights, Ill., USA).

(B) MAP Kinase Inhibitor Effect on the Growth of HL-60 Cells

Figure 4:
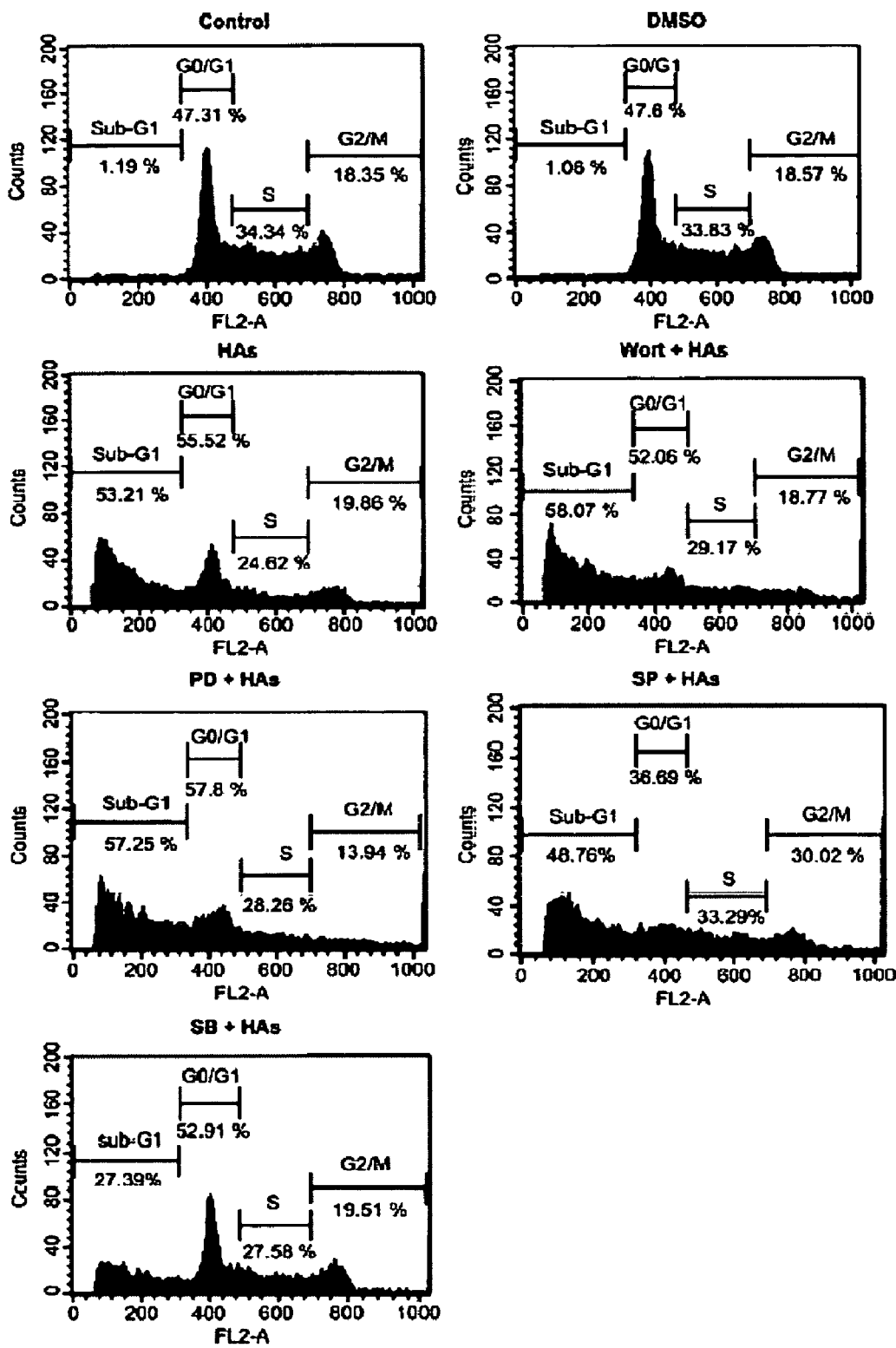
FIG. 4 shows induction of apoptosis by HAs and the effects of various MAP kinase inhibitors. HL-60 cells ($1 \times 10^6$ cells/dish) were preincubated for 24 h with various MAP kinase inhibitors, including SB203580 (SB, 50 AM), SP600125 (SP, 20 AM), PD98059 (PD, 25 AM), and wortmannin (Wort, 1

JNK and p38 kinase activation is known to be associated with the stress-induced apoptosis process, such as anticancer drugs, UV irradiation, and Fas (Butterfield et al., 1997, J. Biol. Chem. 272: 10110; Juo et al., 1997, Mol. Cell. Biol. 17: 24; Seimiya et al., 1997, J. Biol. Chem. 272: 4631). In order to determine which pathway is involved in the HAs-induced apoptosis in HL-60 cells, the effects of three highly specific MAP kinase inhibitors, PD98059 (MEK inhibitor), SB203580 (p38 inhibitor), and SP600125 (JNK inhibitor) were determined, in HAs-induced apoptosis. In addition, wortmannin, a PI-3K inhibitor, was used and shown to inhibit apoptosis in neoplastic cells (Cantrell, 2001, J. Cell. Sci. 114: 1439). The FACScan analysis was employed to assess the ability of these inhibitors to repress the HAs-induced apoptosis. HL-60 cells treated with 50 AM SB203580 (Kim et al., 2002, Cell Immunol. 220: 96) followed by a 24-h exposure to HAs (3 mg/ml) displayed a significant reduction, ~50%, in the sub-G1 phase as compared to that of HAs alone (from 53.21% to 27.39%) (FIG. 4). Inhibitors, PD98059 (25 AM) (Della Ragione et al., 2002, J. Natl. Cancer Inst. 66: 1191), SP600125 (20 AM) (Gajate et al., 2002, J. Biol. Chem. 277: 41580), and wortmannin (1 AM) (Liu et al., 1998, J. Immunol. 160: 1393) did not reduce the cytotoxic action of HAs. This result implies that p38 MAP kinase activated by HAs could play a critical role in inducing apoptotic cell death in HL-60.

(C) HAs Effect on MAP Kinase Family Proteins

To elucidate the involvement of various p38, c-Jun, and ERK signaling components, the expression of candidate signaling molecules was measured upon HAs stimulation. Incubation of HL-60 cells with HAs (3 mg/ml) led to a time-dependent phosphorylation of p38. Phosphorylated p38 could be detected 15 min after HAs addition and remained elevated up to 360 min at 2.68-fold (FIG. 5, upper panel). In addition, the data showed increased phosphorylation of c-Jun in HL-60 cells after stimulation with HAs (3 mg/ml) that was occurred at 30 min and reached the maximal level (~2.59-fold of control) at 360 min (FIG. 5, middle panel). ERK1/2, a kinase been suggested to play a role in survival pathway, therefore showed no phosphorylation upon exposure to HAs (FIG. 5, bottom panel). These data suggested that the activation of p38 and c-Jun kinases was a primary effect during HAs-induced apoptosis in HL-60 cells.

Example 6

(A) Reverse Transcription Polymerase Chain Reaction (RT-PCR)

Total RNA was isolated from cells using a guanidium chloride procedure. cDNA synthesis and PCR amplification were performed as previously described (Hsieh et al., 2004, Arthroscopy 20: 482). For reverse transcription, 4 µg of total cellular RNA were used as templates in a 20-µl reaction containing 4 µl dNTPs (2.5 mM), 2.5 µl Oligo dT (10 pmole/µl), and RTase (200 U/µl), and the reaction was performed at 42° C. for 1 h. Afterwards, 5-µl cDNA was used as templates in PCR amplifications together with appropriate primers. The Fas primers were Forward: 5'-CAAGTGACTGACAT-CAACTCC-3' and Reverse: 5'-CTATTTTGG CTTCAT-TGACACC-3', which amplified a fragment of 727 bp. Each PCR cycle for human Fas consisted of denaturation at 94° C. for 1 min, annealing at 60° C. for 1 min, and elongation at 72° C. for 2 min for a total of 30 cycles. The FasL primers were Forward: 5'-GGAT TGGGCCTGGGGATGTTTCA-3' and Reverse: 5'-TTGTGGCTCAG GGGCAGGTTGTTG-3', which amplified a fragment of 344 bp. Each PCR cycle for human FasL consisted of denaturation at 94° C. for 1 min, annealing at 63° C. for 1 min, and elongation at 72° C. for 2 min for a total of 25 cycles. Glyceraldehyde-3-phosphate dehydrogenase (GAPDH) mRNA served as an internal control. The GAPDH primers were Forward: 5'-CGGAGT-CAACGGATTTGGTCGTAT-3' and Reverse: 5'-AGCCT TCTCCATGGT TGGTGAAGAC-3', which amplified a fragment of 304 bp. Each PCR cycle for GAPDH consisted of denaturation at 94° C. for 1 min, annealing at 65° C. for 1 min, and elongation at 72° C. for 2 min for a total of 25 cycles. The PCR products were visualized on 2% agarose gels stained with ethidium bromide.

(B) HAs-Induced Apoptosis in HL-60 Cells Involves the Release of Apoptosis-Related Proteins from the Mitochondria The involvement of Fas receptor/ligand system has been proposed to mediate apoptosis induced by many anticancer drugs (Friesen et al., 1996, Nat. Med. 2: 574). It was first analyzed whether HAs-induced apoptosis could involve the expression of Fas receptor and its natural ligand. Western blotting analysis showed that Fas expression increased to about 1.78-fold of control after HAs exposure (3 mg/ml) for 360 min. The same treatment condition also induced the expression of the ligand to about 2.38-fold (FIG. 6A). Accordingly, it was suspected that p38 could regulate Fas and FasL transcription via c-Jun. Therefore, the mRNA levels of Fas and FasL were measured by using RT-PCR analysis. The data showed that HAs markedly induced cellular expression of Fas and FasL mRNA that reached the maximal level of about 2.15- and 3.45-fold within 360 min, respectively (FIG. 6B).

Caspases play a pivotal role during apoptosis after treatment with an inducing agent. Immunoblot analysis was used to understand if caspases were activated by HAs in HL-60 cells. Caspase-8 and caspase-3 expression was examined next. The level of cleaved caspase-8 protein increased to 1.78-fold upon the treatment of 3 mg/ml HAs. In contrast, the pro-caspase-8 level decreased (to about 0.62-fold) (FIG. 7). Caspase-3, a downstream effector of caspase-8, also revealed an activation, as shown by the appearance of the p17/20 active form that was increased to 2.93-fold after the exposure of HAs (3 mg/ml) for 360 min. This induction in capase-3 was accompanied by a decrease in pro-caspase-3 (about 0.59-fold) (FIG. 7). These data suggested that caspase-8 mediated the HAs-induced caspase-3 activation.

Example 7

(A) Preparation for Cytosolic and Mitochondrial Fraction

Subcellular fractionation was performed as follows. The cells were washed with TBS, and then cold buffer A (20 mM Tris, 0.03 mM $Na_3VO_4$, 2 mM $MgCl_2 \times 6H_2O$, 2 mM EDTA, 0.5 mM EGTA, 2 mM PMSF, 1 mM DTT, 250 mM sucrose, 10 µg/ml leupeptin) was added. The cells were harvested and carefully homogenized using a homogenizer (Eyela Nazelax) on ice. The lysate was centrifuged at 50,000 rpm, 4° C. for 1 h. The supernatant was collected and used as the cytosol fraction. The pellet was solubilized with buffer B (20 mM Tris, 0.03 mM $Na_3VO_4$, 5 mM $MgCl_2 \times 6H_2O$, 2 mM EDTA, 0.5 mM EGTA, 2 mM PMSF, 1 mM DTT, 5 mM NaF, 10 µg/ml leupeptin, and 0.1% Triton X-100) at 4° C. and mixed by homogenizer (Eyela Nazelax) on ice approximately 10 min to extract mitochondria proteins. Samples were recentrifuged at 50,000 rpm, 4° C. for 1 h, and the supernatant was used as the mitochondrial fraction. Cytochrome c proteins in the two fractions were analyzed with immunoblot and densitometer.

(B) Bid Mediates Release of Mitochondrial Cytochrome c into the Cytosol

Bcl-2 family proteins have exhibited a complex network that regulates apoptosis in multiple biological systems. The cellular levels of Bcl-2, Bax, and Bid in HL-60 cells treated with HAs for 24 h were examined. The expression of Bcl-2 and Bax proteins showed no changes (FIG. 8A) because the HAs-triggered apoptosis was mediated by caspase-8/-3 cascade, and Bid was a proapoptotic Bcl-2 family protein that was activated by caspase-8 in response to Fas/TNF-R1 death receptor signals. Activated Bid (named as tBid) is translocated into the mitochondria and induces cytochrome c release, which in turn activates downstream caspases (Yin, 2000, Cell Res. 10: 161). Thus, it was wondered whether HAs could trigger Bid activation and mitochondrial cytochrome c release. Bid/tBid levels were tested by using a polyclonal anti-Bid antibody that detects both the 23-kDa intact form and the 15-kDa truncated form of the active Bid. The cellular level of the cleaved fragment of p15 active form of Bid increased to 3.86-fold after exposed to HAs (3 mg/ml) for 360 min. In contrast, the level of full-length Bid (p23) decreased (FIG. 8A). The effect of on Bid/tBid was in a time-dependent manner (FIG. 8B). It was next examined whether mitochondrial cytochrome c was released into cytosol using Western blot analysis. Mitochondrial fractions were purified as described previously, and cytochrome oxidase subunit IV (COX 4) levels were used as a control protein to show equal amounts of protein loads (Marchenko et al., 2000, J. Biol. Chem. 275: 16202). As shown in FIG. 8C, HAs treatment caused an accumulation of cytochrome c in the cytosolic fraction, compared to that of control cells, accompanied with a reduction in the mitochondrial fraction in a concentration-dependent manner. After 12 h of treatment, a decrease in cytochrome c in the mitochondria (about 0.63-fold) and an accumulation in the cytosol (about 2.10-fold) were clearly observed (FIG. 8D). Taken together, these results indicated that the cell death caused by HAs were dependent on Bid activation and cytochrome c release in HL-60 cells.

Example 8

Effects of SB203580 in the HAs-Induced Apoptosis

The effects of specific inhibitor of p38, SB203580 on repressing HAs-mediated apoptosis were illustrated in FIGS. 4 and 5. It was supposed that this inhibitor might also suppress the downstream effectors of p38, c-Jun, Fas, and FasL, which are involved in the HAs-induced apoptosis. As shown in FIG. 9, HL-60 cells treated with HAs (3 mg/ml) alone showed significantly elevated levels of c-Jun, Fas, and FasL (lane 2) compared with lane 1. These pretreatment of HL-60 cells with SB203580 (50 AM) was down-regulated by the expressions of these proteins (lane 3). These results again emphasize an important role for p38 activation involved in the HAs-induced apoptosis pathway.

Example 9

HAs-Induced Apoptosis Signaling Pathway Model

The invention was schematically presented in FIG. 10. HAs induced apoptosis via activating p38 MAP kinase that subsequently phosphorylates target protein c-jun and transduced the signal to further activate the apoptotic protein cascades that contained Fas-mediated signaling (Fas/caspase-8/tBid signaling module). As an outcome to the events, cytochrome c released from the mitochondria, leading to the cleavage of caspase-3.

Example 10

Animal Model

The male 49-day-old S-D rats were divided into different groups including negative control, positive control and experimental groups. The positive control rats were intravenous injected with 35 mg/kg NMU (N-Nitroso-N-Methylurea), and the experimental rats were intravenous injected with 35 mg/kg NMU and the HAs (0.1% and 0.2%, respectively). Every group contained 12 rats, totally 48 rats in this experiment. These rats were intravenous injected 1 time per 2 weeks, total 6 times. After injecting 6 times, the rats were observed another 150 days and the body weight and the blood analysis were recorded.

The pathological analysis of the rat liver and spleen were shown in FIGS. 11, 12 and 13. The blood analysis was shown in FIG. 14 and the body weight was shown in FIG. 15.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method for treating a patient suffering from leukemia consisting of administering to the patient a composition consisting of a therapeutically effective amount of an extract of anthocyanins extracted from *Hibiscus sabdariffa* L.

2. The method as claimed in claim 1, wherein the administration is injection, oral or topical.

3. The method as claimed in claim 2, wherein the administration is injection.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(21)
<223> OTHER INFORMATION: forward primer of Fas

<400> SEQUENCE: 1
```

-continued caagtgactg acatcaactc c                                    21

<210> SEQ ID NO 2
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(22)
<223> OTHER INFORMATION: reverse primer of Fas

<400> SEQUENCE: 2
ctattttggc ttcattgaca cc                                   22

<210> SEQ ID NO 3
<211> LENGTH: 23
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(23)
<223> OTHER INFORMATION: forward primer of FasL

<400> SEQUENCE: 3
ggattgggcc tggggatgtt tca                                  23

<210> SEQ ID NO 4
<211> LENGTH: 24
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(24)
<223> OTHER INFORMATION: reverse primer of FasL

<400> SEQUENCE: 4
ttgtggctca ggggcaggtt gttg                                 24

<210> SEQ ID NO 5
<211> LENGTH: 24
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(24)
<223> OTHER INFORMATION: forward primer of GAPDH

<400> SEQUENCE: 5
cggagtcaac ggatttggtc gtat                                 24

<210> SEQ ID NO 6
<211> LENGTH: 25
<212> TYPE: DNA
<213> ORGANISM: Artificial
<220> FEATURE:

```
-continued

<223> OTHER INFORMATION: primer
<220> FEATURE:
<221> NAME/KEY: primer
<222> LOCATION: (1)..(25)
<223> OTHER INFORMATION: reverse primer of GAPDH

<400> SEQUENCE: 6
agccttctcc atggttggtg aagac                                          25
```